(12) United States Patent
Fafiani et al.

(10) Patent No.: US 10,898,124 B1
(45) Date of Patent: Jan. 26, 2021

(54) WEARABLE DEVICE FOR RECORDING MOTION DATA

(71) Applicant: Global Kinetics Pty Ltd, Melbourne (AU)

(72) Inventors: Brendan Fafiani, Port Melbourne (AU); Richard Walker, Wheelers Hill (AU); Rod Wiebenga, Cremorne (AU); Richard Byers, Cremorne (AU)

(73) Assignee: Global Kinetics Pty Ltd, Melbourne (AU)

( * ) Notice: Subject to any disclaimer, the term of this patent is extended or adjusted under 35 U.S.C. 154(b) by 0 days.

(21) Appl. No.: 16/522,115

(22) Filed: Jul. 25, 2019

(51) Int. Cl.
*A61B 5/00* (2006.01)
*G08B 21/24* (2006.01)
*A61B 5/11* (2006.01)
*G08B 7/06* (2006.01)

(52) U.S. Cl.
CPC .......... *A61B 5/4082* (2013.01); *A61B 5/0002* (2013.01); *A61B 5/1101* (2013.01); *A61B 5/112* (2013.01); *A61B 5/1118* (2013.01); *A61B 5/4809* (2013.01); *A61B 5/4815* (2013.01); *A61B 5/4833* (2013.01); *A61B 5/681* (2013.01); *A61B 5/743* (2013.01); *A61B 5/7405* (2013.01); *A61B 5/7455* (2013.01); *G08B 7/06* (2013.01); *G08B 21/24* (2013.01); *A61B 2560/0214* (2013.01); *A61B 2562/0219* (2013.01)

(58) Field of Classification Search
CPC .......... A61B 5/40; A61B 5/0002; A61B 5/11; A61B 5/681; A61B 5/1101; A61B 5/7405; A61B 5/743; A61B 5/112; A61B 2560/0214; A61B 2562/0219; A61B 5/7455; A61B 5/4815; A61B 5/1118; G08B 21/24; G08B 7/06
See application file for complete search history.

(56) References Cited

U.S. PATENT DOCUMENTS

| | | | |
|---|---|---|---|
| 2012/0089000 A1* | 4/2012 | Bishay | A61B 5/02438 600/391 |
| 2013/0120106 A1* | 5/2013 | Cauwels | G06F 1/163 340/3.1 |
| 2016/0367187 A1* | 12/2016 | Ahmed | A61B 5/02405 |

* cited by examiner

*Primary Examiner* — Patrick Fernandes
(74) *Attorney, Agent, or Firm* — Banner & Witcoff, Ltd.

(57) ABSTRACT

A wearable device comprising a data logger, a motion sensor, and a memory component is disclosed for recording motion data. The motion sensor may detect movement of the device when worn by a subject, and the memory component may store motion data from the motion sensor. A casing may be included for retaining the data logger and providing a contact barrier between at least part of the data logger and the subject. The contact barrier may substantially prevent contact contamination of at least part of the data logger while the device is worn by the subject for collection and storage of subject-specific motion data. The casing is controllably accessible to release the data logger in a substantially uncontaminated state.

25 Claims, 13 Drawing Sheets

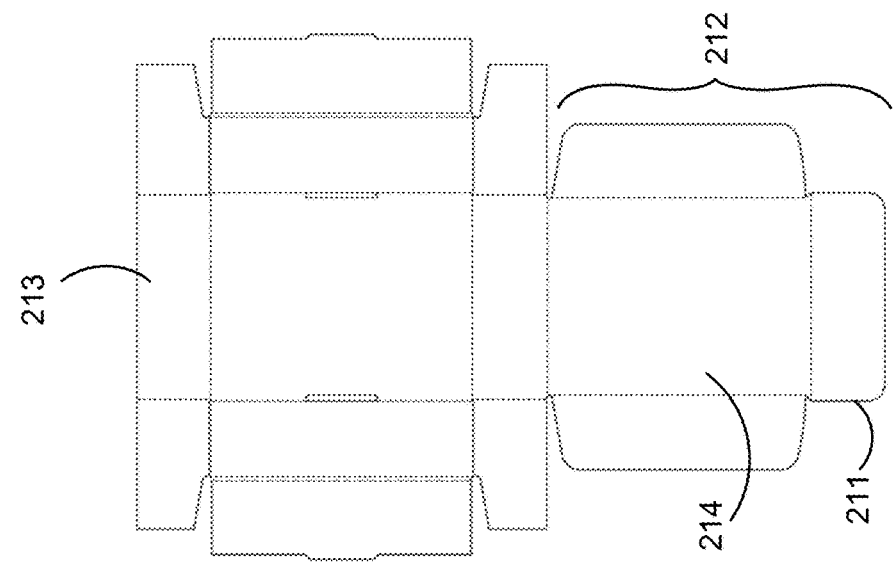
Fig. 4C
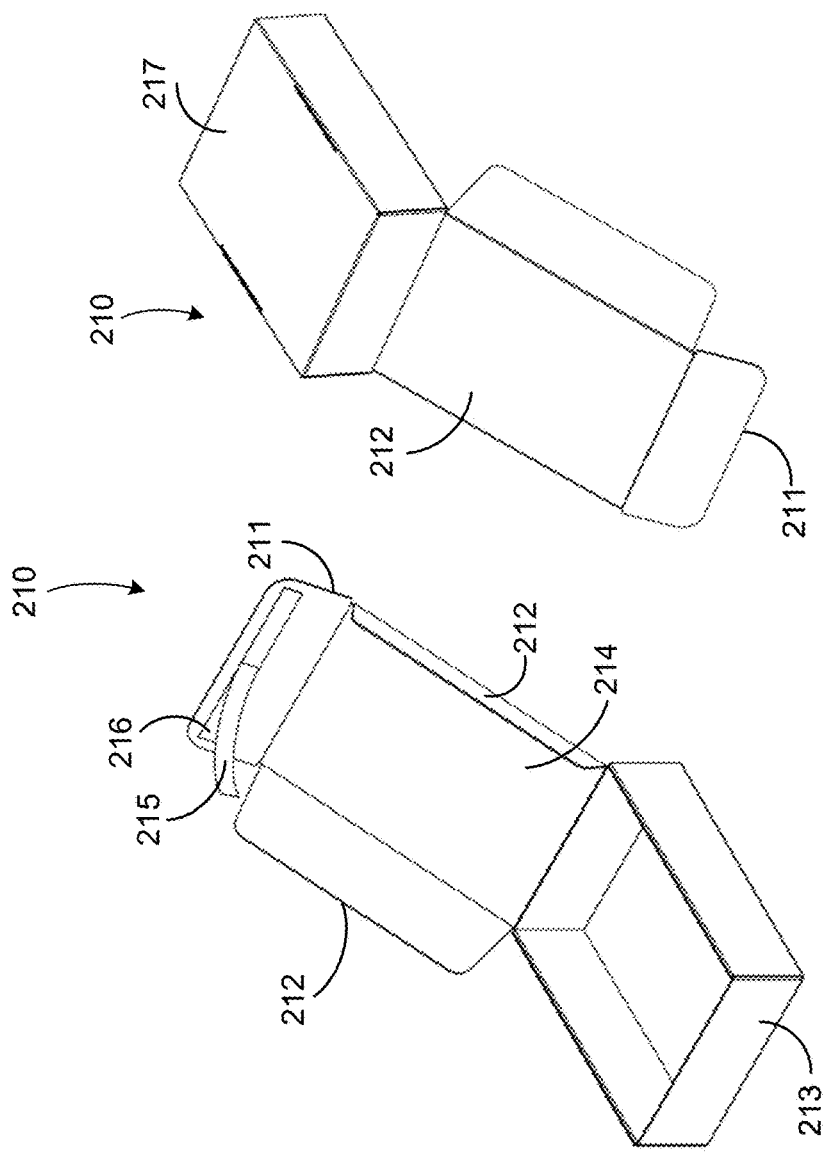
Fig. 4B
Fig. 4A

Patient: ████████
Record Number: 12345
Deep Brain Stimulation: No
Infusion Therapy: None
Reason for PKG: --

Medication: --

 PKG Inconclusive — Insufficient data to draw clear conclusions.

Longitudinal View - Dyskinesia

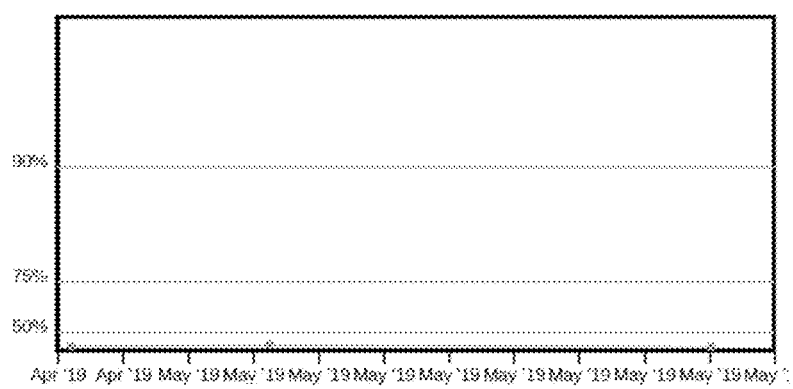

PKG 1: May 09, 2019
DKS: 0.3 - 0.9 - 3.2
Medication: --

PKG 2: May 02, 2019
DKS: 0.5 - 1.4 - 5.1
Medication: --

PKG 3: Apr 29, 2019
DKS: 0.4 - 1.0 - 3.0
Medication: --

Longitudinal View - Bradykinesia

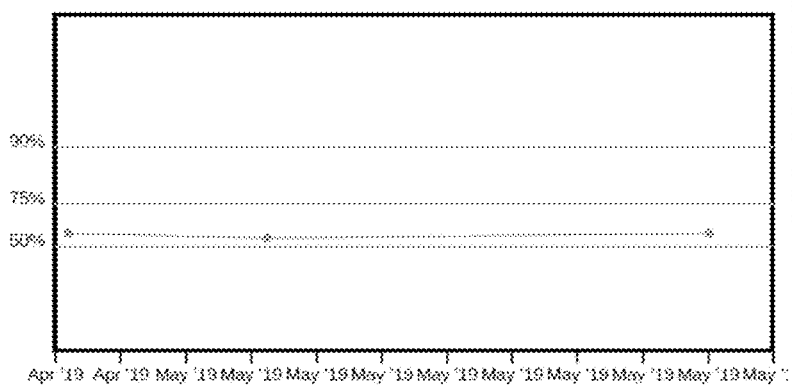

PKG 1: May 09, 2019
BKS: 13.5 - 20.9 - 26.7
Medication: --

PKG 2: May 02, 2019
BKS: 13.5 - 20.0 - 26.5
Medication: --

PKG 3: Apr 29, 2019
BKS: 14.3 - 20.9 - 29.4
Medication: --

Longitudinal View - Additional Results

| Parameter | Current PKG | PKG 2 | PKG 3 |
|---|---|---|---|
| Median Bradykinesia Score (BKS) | 20.9 | 20.0 | 20.9 |
| Median Dyskinesia Score (DKS) | 0.9 | 1.4 | 1.0 |
| Fluctuation DKS (FDS) | 5.3 | 5.1 | 5.1 |
| % Time Tremor (PTT) | 5.5% | 4.4% | 7.8% |
| % Time Immobile (PTI) | 1.3% | 1.0% | 0.9% |

The quantitative scores in this chart are calculated from the data collected in the reference period of 09:00-18:00

PKG Notes

No significant change from previous PKGs

Fig. 8E

Patient: ███████████
Year of Birth: 1970
Record Number: 12345
Physician: Chris Schreurs
Clinic: my-test
Session Duration: 6 Days
Session Start: May 09, 2019
Reason for PKG: --

Medication: --
Deep Brain Stimulation: No
Infusion Therapy: None

PKG Inconclusive

Insufficient data to draw clear conclusions.

Findings Summary

Factors Limiting Interpretation

No factors limiting interpretation.

Daily Plots

No significant day-to-day change.

Dyskinesia + Bradykinesia Daytime Session Averages

Median BKS within target range for most of the day.

No significant DKS

Daytime Patient Results

DKS at 35th percentile of controls.

BKS within control range and optimal target range (-23)

Significant tremor present

Daytime Tremor Summary

Significant tremor present - no correlation with medication reminder times.

Daytime Immobility Summary

No significant daytime immobility.

Peri Dose

No significant dose-dependant effects.

Longitudinal View - Additional Results

No significant change from previous PKGs

Clinician Notes

PKG prescribed for follow-up patient visit

No treatment change made

Patient probably needs to spend less time in the office and more time outside.

Fig. 8F

WEARABLE DEVICE FOR RECORDING MOTION DATA

TECHNICAL FIELD

The present disclosure relates to a wearable device for recording motion data. It relates particularly, but not exclusively, to a wearable device and an associated kit and system for use in assessment of movement disorders in a continuous, passive (i.e. non-task based), remote fulfillment model where the subject being assessed is ambulatory and able to continue daily living during recording.

BACKGROUND OF THE ART

A broad range of movement disorders exist. Parkinson disease (PD) is one of the most prevalent, affecting over 6 million people globally. PD is a progressive disorder of the nervous system, affecting the frontal lobe of the brain which controls impulsive and non-impulsive movement. People with PD have less dopamine, a neurotransmitter released by brain neurons in the part of the brain which helps regulate movement. People with PD experience movement related symptoms such as bradykinesia, rigidity, tremor and postural instability. Non-movement symptoms may include speech and swallowing difficulties, cognitive impairment or behavioural change, and sleep disturbance.

Skilled neurologists can detect the presence of bradykinesia and dyskinesia and provide a measure of its severity. However this is inherently subjective and scores may vary between different periods of observation performed by a single neurologist and there can be differences in scores given by different neurologists. Furthermore, this assessment can only be done when the neurologist is with the patient, whereas the response to treatment with drugs such as Levodopa or L-Dopa may fluctuate over the course of the day and from day to day and thus continuous objective monitoring is desirable.

While experienced clinicians can usually detect and estimate the severity of bradykinesia and other movement disorders during a period of observation, these disorders are not easily quantified making disease management and medication management challenging. Moreover, a period of observation in the clinic is finite (typically a period of 10 or so minutes) usually requires the subject to undertake some clinician-directed motor tasks and is undertaken in an environment that is not familiar to the patient, potentially altering or exacerbating symptoms from what is experienced in day-to-day life. Self-reporting of symptoms by patients can do away with the environmental problem but this can be unreliable and is also subjective.

Objective monitoring of movement disorders using a wearable device would enable clinicians to diagnose and evaluate disease state and progression more precisely. It would also assist clinicians to establish e.g. when the management of PD using L-Dopa related oral therapies was failing and required advanced therapies such as deep brain stimulation (DBS) to maintain good control of symptoms.

Wearable devices exist for the collection of movement related data however these are not convenient for use in the assessment of more than one subject due to the risk of transferring bioburden between subjects. Cleaning can be performed however this is inconvenient and may damage the device.

It would be desirable to provide device that overcomes or ameliorates one or more of the problems associated with known approaches to monitoring movement disorders such as Parkinson's disease.

The discussion of the background included herein including reference to documents, acts, materials, devices, articles and the like is included to explain the context of the present disclosure. This is not to be taken as an admission or a suggestion that any of the material referred to was published, known or part of the common general knowledge any other country as at the priority date of any of the claims.

BRIEF SUMMARY

Viewed from one aspect, the present disclosure provides a wearable device for recording motion data, the device comprising: a data logger having a battery, a motion sensor configured to detect movement of the device when worn by a subject, and a memory component configured to store motion data from the motion sensor; a casing for retaining the data logger and providing a contact barrier between at least part of the data logger and the subject; and a strap attached to or integral with the casing for wearing by the subject; wherein the contact barrier substantially prevents contact contamination of at least part of the data logger while the device is worn by the subject for collection and storage of subject-specific motion data, and wherein the casing is controllably accessible to release the data logger in a substantially uncontaminated state.

In some embodiments, the data logger includes contact couplings for coupling with a docking station or cable, and wherein the contact couplings are inaccessible when the data logger is retained in the casing.

In some embodiments, the data logger includes a screen and the device includes a transparent protector providing a contact barrier between the screen and the subject. The wearable device may include a bezel configured to releasably couple with one or both of the data logger and the casing, the bezel, casing and transparent protector substantially preventing contact contamination of the data logger including the screen by the subject.

In some embodiments, the data logger includes a processor that is configurable to present the subject with one or medication reminders based on subject-specific parameters received during configuration of the device. The data logger includes one or more of: a loudspeaker and the one or more medication reminders are presented in the form of an audible prompt emitted from the loudspeaker; a screen and the one or more medication reminders are presented in the form of a visible prompt presented on the screen; and a vibrating element and the one or more medication reminders are presented in the form of a haptic prompt presented by the vibrating element.

In some embodiments, the data logger is configurable to communicate with an external processor via the one or more contact couplings, and the external processor is adapted to perform one or more of: configuring the data logger for wear by a subject during an assessment period; processing motion data stored by the data logger; generating a report based on processed motion data from the data logger; reconditioning the data logger after wear by the subject. Alternatively/additionally, communication between the data logger and an external processor may be by wireless communication means.

In some embodiments, the data logger and/or its component parts is adapted to be refurbished or recycled.

In some embodiments, the casing and the band are disposable or recyclable.

In some embodiments, the data logger is operable for continuous recording of motion data that is indicative of the presence or absence of movement disorder symptoms and behaviours selected from a group including: bradykinesia, dyskinesia, tremor, fluctuations, immobility, daytime somnolence, medication adherence, daytime sleep, night-time sleep, sleep duration, sleep quality and gait.

In some embodiments, the data logger is operable for continuous recording of motion data for a minimum of 72 hours and up to at least 10 days.

In some embodiments, the data logger includes a sensor for determining if the device is being worn by the subject.

Viewed from another aspect, the present disclosure provides a kit for recording motion data, the kit comprising: a wearable device comprising a data logger having a battery, a motion sensor configured to detect movement of the device when worn by a subject, a memory component configured to store motion data from the motion sensor, a casing for retaining the data logger and providing a contact barrier between at least part of the data logger and the subject, and a strap attached to or integral with the casing for wearing by the subject; a tray for receiving the wearable device; and a carton for housing the tray and the wearable device during delivery of the wearable device to and from the subject, the carton having a fastening portion operable by the subject to fasten the carton closed for delivery of the device, storing motion data from the subject, to a recipient.

In some embodiments, the tray is moulded to receive one or more accessories for the wearable device, the accessories including but not limited to: a cleaning cloth; and a strap extension. The tray may be moulded to receive the casing and strap separately from the data logger.

In some embodiments, the carton has a foldable closure and the fastening portion includes an adhesive with a removable release liner on the foldable closure.

In some embodiments, the carton is pre-marked with a recipient location and postal authority such as a prepaid shipping label, for delivery of the carton and contents from the subject to the recipient location.

In some embodiments, the carton includes a foldable lid having an inside panel displaying one or both of instructions for use of the device and instructions for sending the used device storing motion data from the subject, in the carton, to the recipient.

In some embodiments, the data logger has a screen and the wearable device includes a bezel and a transparent protector providing a contact barrier between the screen and the subject, the bezel being configured to couple with one or both of the data logger and the casing, wherein the bezel and the transparent portion substantially prevent contact contamination by the subject of the data logger including the screen.

In some embodiments, the data logger is adapted to be removed from the casing by the recipient.

In some embodiments, the data logger and/or its component parts is adapted to be refurbished or recycled.

Viewed from another aspect, the present disclosure provides a system for recording motion data for a subject, the system comprising: a wearable device comprising: a data logger having a battery, a motion sensor configured to detect movement of the device when worn by a subject, a memory component storing motion data from the motion sensor and a casing for retaining the data logger and providing a contact barrier between at least part of the data logger and the subject; a configuration terminal comprising a processor and a communicative coupling adapted to communicate with the data logger, the configuration terminal being operable to configure the data logger to record motion data for a specific subject; and an analysis terminal comprising a processor and a communicative coupling adapted to communicate with the data logger, the analysis terminal being operable to extract subject-specific motion data stored on the data logger and generate one or more subject-specific reports from the extracted data which present objective characteristics of the movement data recorded for the specific subject; wherein the casing is controllably accessible to release the data logger in a substantially uncontaminated state.

In some embodiments, the configuration terminal configures the data logger by transmission, through the communicative coupling, of a configuration file containing configuration data pertaining to one or more of: prescribing or treating clinician; subject; body location of the device during wear; medication prescribed to the subject; and concurrent therapies including device assisted therapies.

In some embodiments, objective characteristics presented in reports generated by the analysis terminal include: graphs charting bradykinetic and/or dyskinetic behaviour over time; values representing amount or proportion of time spent in one or more of bradykinesia, dyskinesia, tremor, immobile, inactive, active; values representing a bradykinesia or dyskinesia score, quality of sleep, and sleep fragmentation; number of steps taken; medication dosage compliance; fluctuations; device assisted therapy suitability; quality of sleep; medication reminders provided; medication acknowledgements; and target ranges for one or more objective parameters contained in the report, such as bradykinesia and dyskinesia.

In some embodiments, the data logger has one or more contact couplings for coupling with one or both of the configuration terminal and the analysis terminal using a cable or docking station, and the contact couplings are inaccessible when the data logger is retained in the casing.

In some embodiments, the system includes a tool for releasing the data logger from the casing.

It is to be noted that any one of the aspects mentioned above may include any of the features of any of the embodiments of other aspects mentioned above and may include any of the features of any of the embodiments described below, as appropriate.

It is to be understood each of the various aspects described herein may incorporate features, modifications and alternatives described in the context of one or more other aspects, such as but not limited to the various features and functions of a wearable device, a kit, a system, a data logger, a tool, a carton, a tray and the like. For efficiency, such features, modifications and alternatives have not been repetitiously disclosed for each and every aspect although one of skill in the art will appreciate that such combinations of features, modifications and alternatives disclosed for some aspects apply similarly for other aspects and are within the scope of and form part of the subject matter of this disclosure.

BRIEF DESCRIPTION OF DRAWINGS

The present disclosure will now be described in greater detail with reference to the accompanying drawings. It is to be understood that the embodiments shown are examples only and are not to be taken as limiting the scope of the invention as defined in the claims appended hereto.

FIG. 4A is an isometric view from above, of a carton for a kit according to an embodiment of the disclosure. FIG. 4B is an isometric view from below, of the carton of FIG. 4A. FIG. 4C is a top view of a blank for the carton in FIGS. 4A and 4B.

FIGS. 8A to 8F are examples of pages of a report generated by a system according to embodiments of the disclosure.

DETAILED DESCRIPTION

Figure 1A:
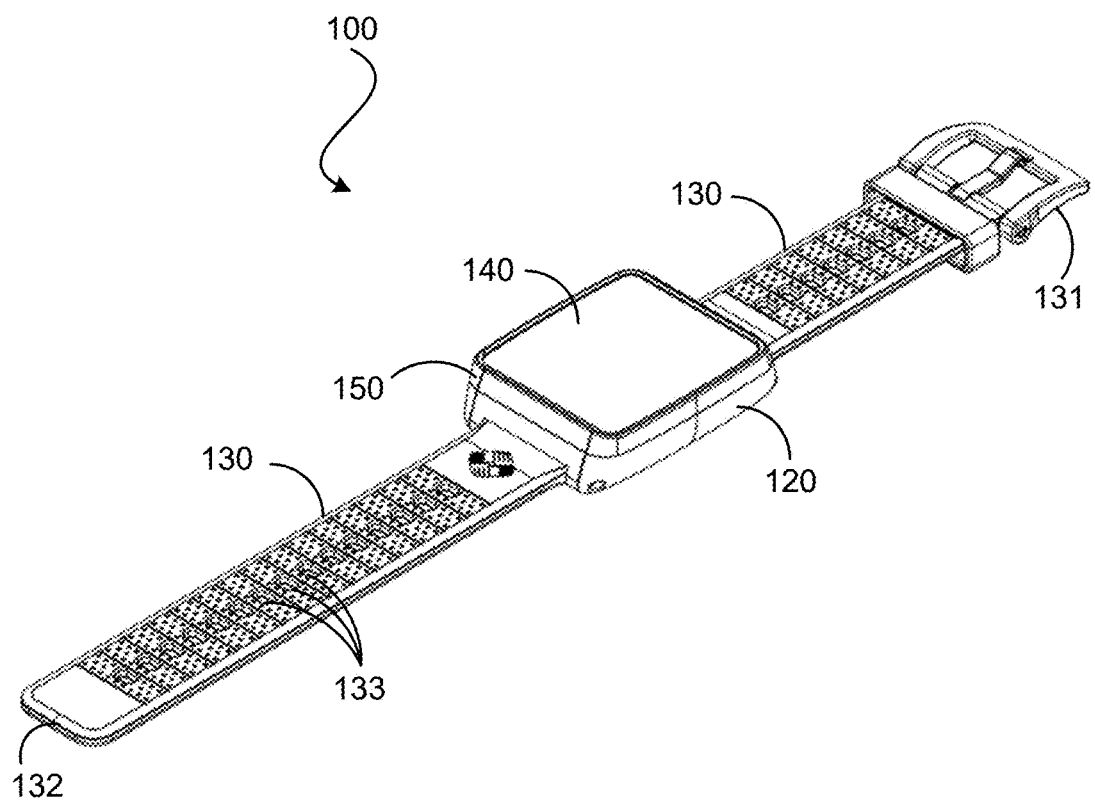
FIG. 1A is an isometric view from above, of a wearable device according to an embodiment of the disclosure.
Figure 1B:
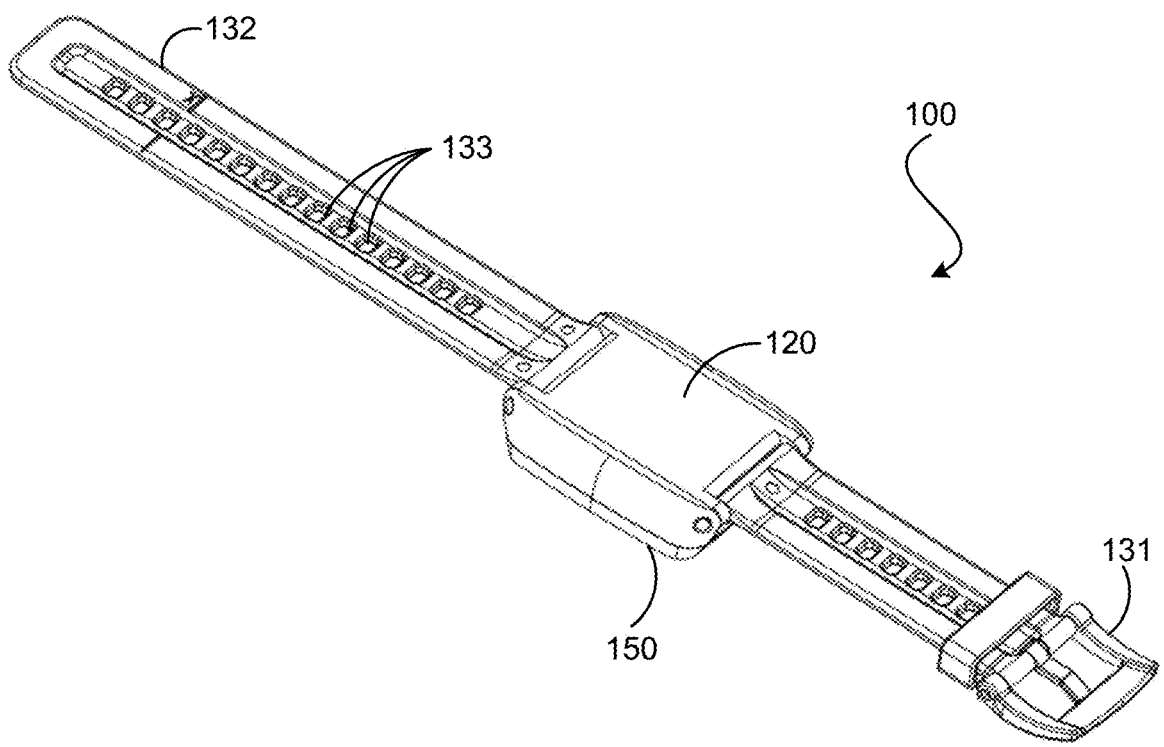
FIG. 1B is an isometric view from below, of the wearable device of FIG. 1A.
Figure 2:
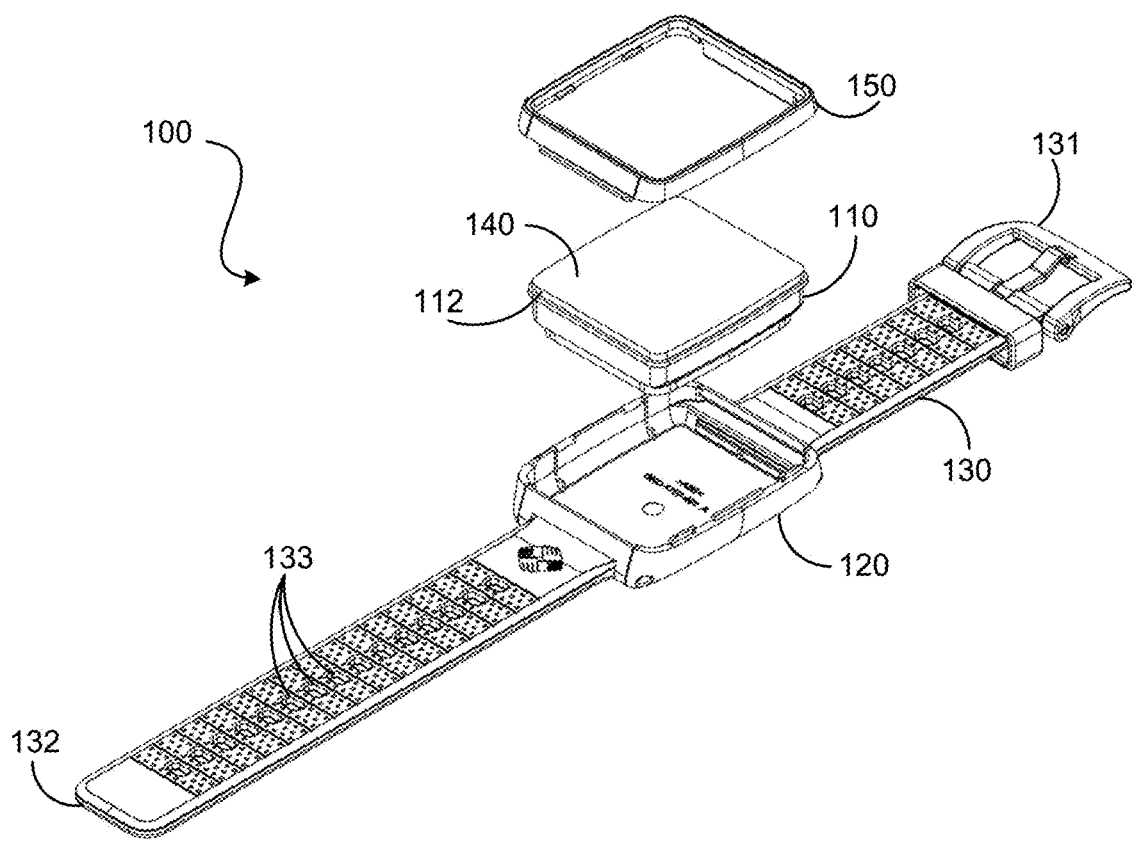
FIG. 2 is an exploded view of the wearable device of FIG. 1A.

Referring firstly to FIGS. 1A, 1B and 2, there is shown a wearable device 100 for recording motion data. The device 100 comprises a data logger 110 having a battery, a motion sensor configured to detect movement of the device when worn by a subject, and a memory component configured to store motion data from the motion sensor. The motion sensor within data logger 110 may comprise any motion sensing element capable of generating an electric output indicative of movement of the subject as detected by motion of the device 100 while worn, e.g. on the subject's wrist. The motion sensor may include, for example, an accelerometer, gyroscope, micro electro mechanical system (MEMS) device or other inertial sensor although it is contemplated that pressure, light and other sensors configurable to detect movement of the device 100 during wear by the subject may be utilised. Data logger 110 may further include a capacitive sensor or other sensor for determining if the logger is being worn by a subject or not. Outputs from the capacitive sensor may be stored by the memory component. Typically, data logger 110 also includes a processor that is configurable to control interoperation of the battery, motion sensor, memory component, capacitive sensor and other functional features of the data logger.

Device 100 further includes a casing 120 for retaining the data logger. In the embodiment illustrated, casing 120 provides a cradle that contains data logger 110 in a manner that provides a contact barrier between the subject wearing the device and the sides and underside of the data logger. The upper surface of data logger 110 includes a screen 112 and the device 100 includes a transparent protector 140 providing a contact barrier between the screen and the subject. Additionally, device 100 includes a bezel 150 which is configured to releasably couple with casing 120, such that the bezel, casing and transparent protector 140 substantially prevent contact contamination of data logger 110 including screen 112 by the subject. In some embodiments, bezel 150 may couple with data logger 110, and these two parts may couple with casing 120 to securely retain the data logger. In numerous examples, the device 100 is substantially tamper proof such that a special tool or skill is required to separate bezel 150 from casing 120 to release data logger 110 from within. It is intended that removal of data logger 110 from casing 120 by hand is difficult, if not impossible for one not in possession of a special tool or skill.

It is to be understood, that casing 120 could completely enclose data logger 110 in a manner that provides a contact barrier precluding physical contact between any part of the data logger and the subject. In some arrangements, casing 120 may be a unitary piece. In other arrangements, casing 120 may comprise two (or more) parts that cooperate to preclude contact between the subject and data logger 110. A casing 120 provided in multiple cooperating parts or a casing cooperating with a bezel 150 as shown in FIGS. 1A, 1B and 2 may incorporate screws, friction fit fasteners or other fasteners that are operable by a tool to release data logger 110 from casing 120 to provide access to subject-specific motion data which is recorded during a period of wear of the device 100 by the subject and stored on the memory component of data logger 110. Ideally access to a tool to release data logger 110 from casing 120 is restricted to entities having permission to access the subject-specific motion data.

Device 100 includes strap 130 which may be attached to or integral with casing 120 for wearing by the subject. Typically, strap 130 is configured for wearing of device 100 to the subject's left or right wrist so that the device may be worn like a watch. Thus, buckle 131 is utilised with tongue 132 and holes 133 to appropriately size and secure device 100 on the subject's wrist. It is to be understood, however, that other fasteners could be adopted such as e.g. hook and loop fastening materials, magnetic fasteners and the like. It is also to be understood that strap 130 may be configured in a manner, or replaced by a fastening that enables device 100 to be worn on a different body area such as the chest, ankle, abdomen, thigh, upper arm or the like.

The contact barrier formed by casing 120, or by casing 120 in conjunction with transparent protector 140 and bezel 150 substantially prevents contact contamination of data logger 110 while the device 100 is worn by the subject for collection and storage of subject-specific motion data. Because casing 120 is controllably accessible requiring a special tool or skill to release data logger 110 in a substantially uncontaminated state, entities who have access to the subject-specific motion data stored on the data logger are not exposed to bio burden that could otherwise be transferred on device 100. Advantageously, this also makes possible recycling or refurbishment of data logger 110 and its component parts as the risk of cross contamination or transfer of bioburden is minimised.

Figure 3:
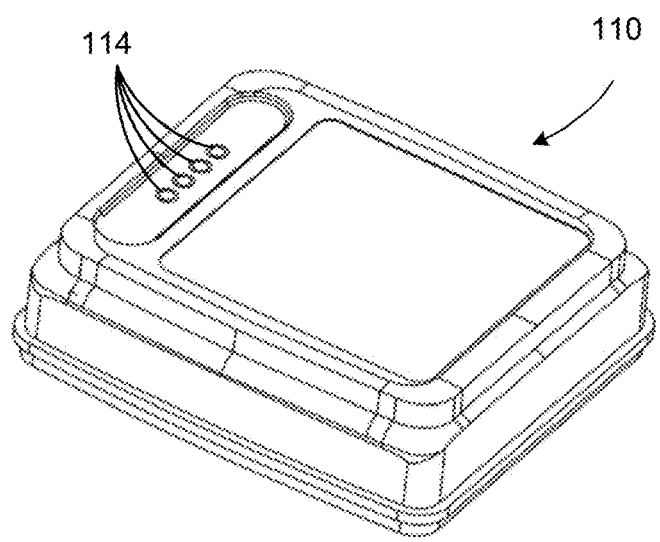
FIG. 3 is an isometric view from below, of a data logger according to an embodiment of the disclosure.

As shown in FIG. 3, data logger 110 includes contact couplings 114 which are provided on the underside for coupling with a docking station or cable. Owing to the casing 120, contact couplings 114 are inaccessible when the data logger is in use by the subject. Thus not only does casing 120 prevent contact contamination of data logger 110 including contact couplings 114, subject-specific data stored on the data logger is protected since access to the contact couplings is restricted to entities who have access to the tool or special skill necessary to release the data logger from the casing. While the embodiment shows contact couplings 114 in the form of four physical contacts, it is to be understood that other data transmission couplings may be adopted into the form of data logger 110, such as a USB socket or the like which is configured to contact and communicatively couple with a corresponding plug, cable or docking station. Further, it is to be understood that as an alternative or in addition to contact couplings 114, data logger 110 may include a component for wireless data transmission e.g. using Bluetooth or other techniques and standards as would be appreciated by one of skill in the art.

In preferred embodiments, the processor of data logger 110 is configurable to present the subject with one or medication reminders based on subject-specific parameters received during configuration of the device. In the embodiment illustrated, the data logger processor is configurable to cause screen 112 to present one or more medication reminders in the form of a visible prompt presented on the screen. This reminder is accompanied by a haptic or vibrational cue that is generated by a vibrating element contained within data logger 110 and controlled by the data logger processor. In some embodiments, data logger 110 may also include a loudspeaker and medication reminders may be presented in the form of an audible prompt emitted from the loudspeaker controlled by the data logger processor.

In numerous examples, the data logger processor is also configurable to receive inputs from the subject. Such inputs may include, for example, a medication acknowledgement indicating that the necessary medication has been consumed. This may follow a medication prompt. In an embodiment where screen 112 is touch sensitive, such an input may be received e.g. by the user swiping a finger across the screen (covered by transparent protector 140), or e.g. depressing an element of casing 120 that in turn actuates a button on data logger 110, thereby avoiding direct contact between the subject and the data logger. Preferably, one or more of the haptic, visible and audible medication reminder prompts are repeated until a medication acknowledgement is supplied to device 100 by the subject. When a medication acknowledgement input is supplied by the subject, the data logger processor may respond by causing presentation of a tick or other display on screen 112, or causing an audible tone or announcement to be presented by the loudspeaker.

When data logger 110 of device 100 is outside the casing 120, it is operable to communicate with one or more external processors via contact couplings 114 although wireless communication may be utilised as described above. An external processor can be utilised to configure data logger 110 for wear by a subject during an assessment period, process subject-specific motion data collected during an assessment period and stored by the data logger 110, and generate one or more reports based on subject-specific motion data stored by the data logger. A single external processor may perform all of these functions, or separate external processors may perform individual functions. It is to be understood that an external processor may be distributed or accessed over a secure network, or may reside in a single secure location.

After release of data logger 110 from casing 120 using a special tool or skill, the casing together with strap 130 may be discarded and disposed of or recycled. The memory component of data logger 110 is accessed by the external processor through contact couplings 114 on the data logger which are connected with a docking station or cable adapted to communicate with the external processor. Once subject-specific data has been extracted from the memory component of data logger 110, the data logger may be returned to the manufacturer for refurbishment or recycling either in its entirety, or in its component parts.

Wearable device 100 enables safe and biohazard free use of data logger 110 for continuous recording of motion data for use in diagnosis and/or analysis of movement disorder symptoms in a subject. These symptoms may include, but are not limited to bradykinesia, dyskinesia, tremor, fluctuations, immobility daytime somnolence, medication adherence and the like. Recorded motion data may also be used to monitor sleep (day time and night time) including duration and quality of sleep, as well as gait and other movement-related behaviours that are not solely experienced by those with movement disorders. Advantageously, recording of motion data using the inventive device is passive, in that the subject is not required to perform particular tasks to determine the presence or absence of certain symptoms. Motion data output by the motion sensor and stored by the memory component may be processed by the external processor using any suitable methodology. One suitable methodology is disclosed in WO2009/149520 entitled "Detection of Hypokinetic and/or Hyperkinetic States", the entire disclosure of which is hereby incorporated herein by reference.

Data logger 110 is operable for continuous recording of motion data. Ideally, to capture a statistically significant set of motion data for the subject, an assessment period involves wear of device 100 and collection of motion data for a minimum of 72 hours and up to at least 10 days, although a period of about 6 days is often considered to be clinically sufficient.

FIGS. 4A to 4C and 6A to 6C relate to a kit 600 for recording motion data. The kit 600 includes a carton 210 for housing a tray 220 and the wearable device 100 during delivery of the wearable device to and from the subject. The carton 210 may have any suitable shape and be manufactured from any material that is sufficiently rigid to prevent damage to the wearable device contained during the usual course of delivery by postal or courier service or the like. Tray 220 also serves to protect device 100 by being moulded to receive the device in a section that effectively immobilises the device inside carton 210. Typically the carton is manufactured from cardboard and the tray is manufactured from a moulded pulp. Use of these materials is advantageous in that they are low cost, lightweight, can be printed upon, manufactured using some recycled materials and can be recycled themselves at the end of their lifecycle. However there are many other suitable materials as would be understood by one of skill in the art.

In numerous examples, tray 220 is moulded to provide a suitably contoured slot 221 for receiving the wearable device 100. Spare slots 222, 223 may be provided to receive accessories for the device such as strap extensions, cloths, folded paper inserts for instructions, patient forms and the like although it is to be understood that such slots need not be occupied even when provided in moulded tray 220. A ledge 224 provided around the internal periphery of tray 220 may be used to support an instruction insert or leaflet within carton 210.

In some embodiments, tray 220 includes slots 221, 223 to receive the strap 130 and casing 120 separately from the data logger 210. In this embodiment, some assembly of the wearable device 100 is required before it can be worn by the subject. Because it is intended for contact access to data logger 110 to be restricted to entities, a kit dispatched in this form is not intended for direct delivery e.g. from the manufacturer to the subject. Rather, it may be sent to a clinic or other entity e.g. for configuration of data logger 110 prior to device 100 being forwarded on to a subject for assessing movement disorder symptoms. In such an arrangement the entity would fasten the configured data logger 110 into the casing 120 and bezel 150 to provide a contact barrier between the data logger and the subject, before returning it to carton 210 and tray 220 for dispatch to the subject.

In the embodiment shown in FIG. 4A, carton 210 has a fastening portion in the form of a lip 211 extending from a lid 212 of the carton. To close carton 210, lip 211 is folded inside the opposing carton wall 213. Lip 210 is operable to close the carton containing the device 100 when it has been configured for use by the subject for recording motion data from the subject for use in e.g. assessment of movement disorder symptoms. Once the device 100 has been configured and enclosed within carton 210, it may be further enclosed within a postal bag or the like for dispatch to the subject. In some embodiments, the carton itself may be dispatched to the subject, without a postal bag.

Upon receipt of carton 210 by the subject, it is opened to reveal the configured device 100 within. In preferred embodiments, the inside surface 214 of lid 212 contains instructions printed directly onto the lid material, or on a label affixed to the inside lid surface, informing the subject on correct use of the device. Instructions may include how to initialise and wear device 100. Ideally, the instructions include directions for returning the device 100 to a recipient. These instructions include directing the subject to place the device 100 storing motion data from the subject into the slot 221 of tray 220 and fasten the carton 210 closed by removing release liner 215 from adhesive strip 216 on the lip 211 before closing the container as described above. Other fastening means such as a tab and slot arrangement are also contemplated and within the scope of the disclosure.

In numerous examples, carton 210 is marked with a recipient location and postal authority for delivery of the carton and its contents from the subject to the recipient location. Thus, a prepaid shipping label may be printed on or affixed to the base 217. Typically, the recipient is an entity who, upon receipt of the carton 210, removes device 100 and utilises a tool to release the data logger 110 containing the subject-specific motion data from the casing 120, and accesses contact couplings 114 to extract the motion data. The casing 120, strap 130, bezel 150 and transparent protector 140 may be discarded or recycled.

Figure 5A:
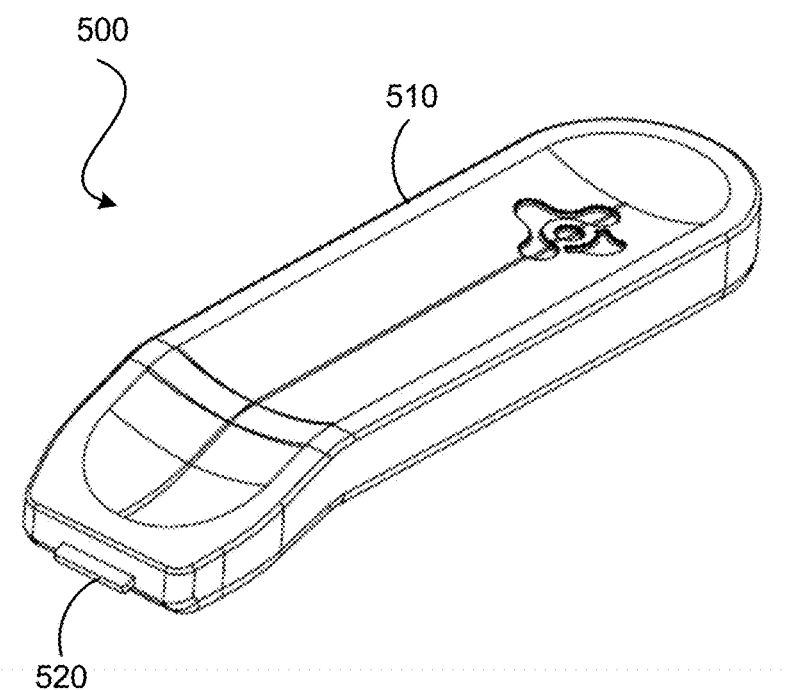
FIG. 5A is an isometric view from above of a tool for accessing a data logger in a wearable device according to an embodiment of the disclosure.
Figure 5B:
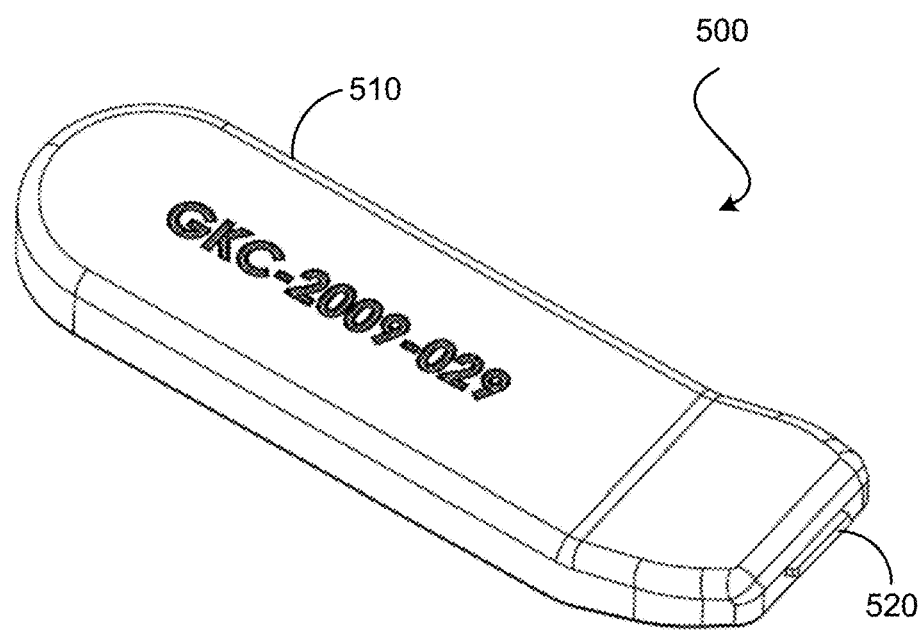
FIG. 5B is an isometric view from below, of the tool of FIG. 5A.
Figure 6A:
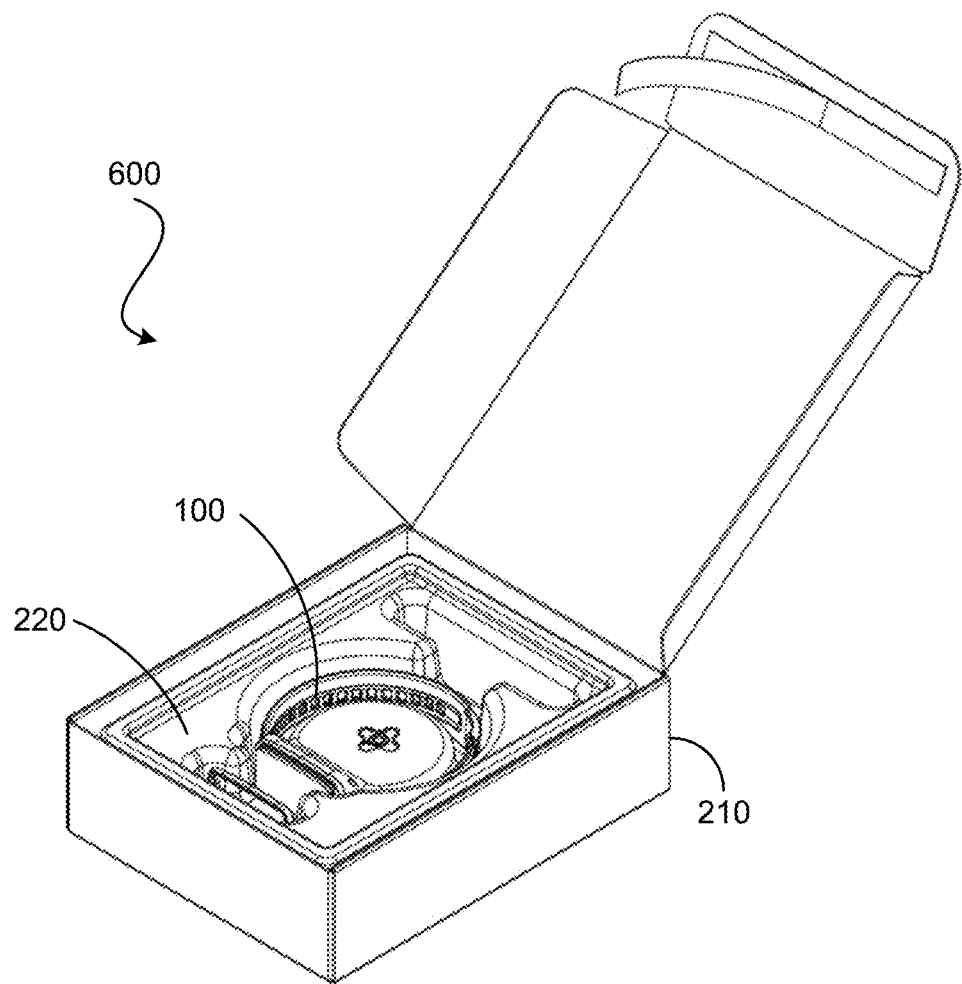
FIG. 6A is an isometric view from above of a kit according to an embodiment of the disclosure.
Figure 6B:
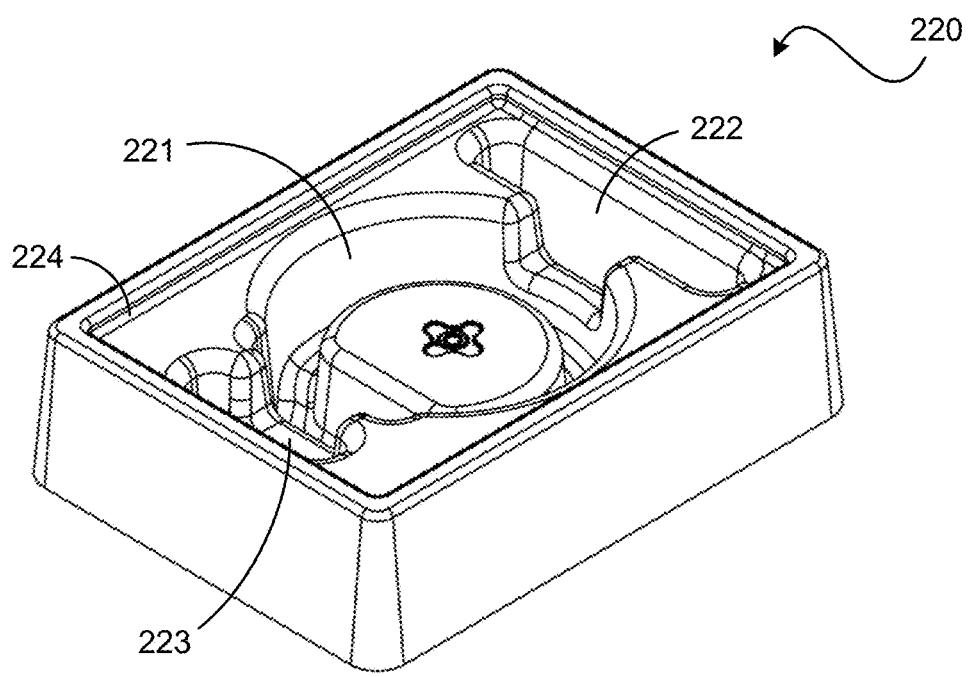
FIG. 6B is an isometric view from above of a moulded tray of a kit according to an embodiment of the disclosure.
Figure 6C:
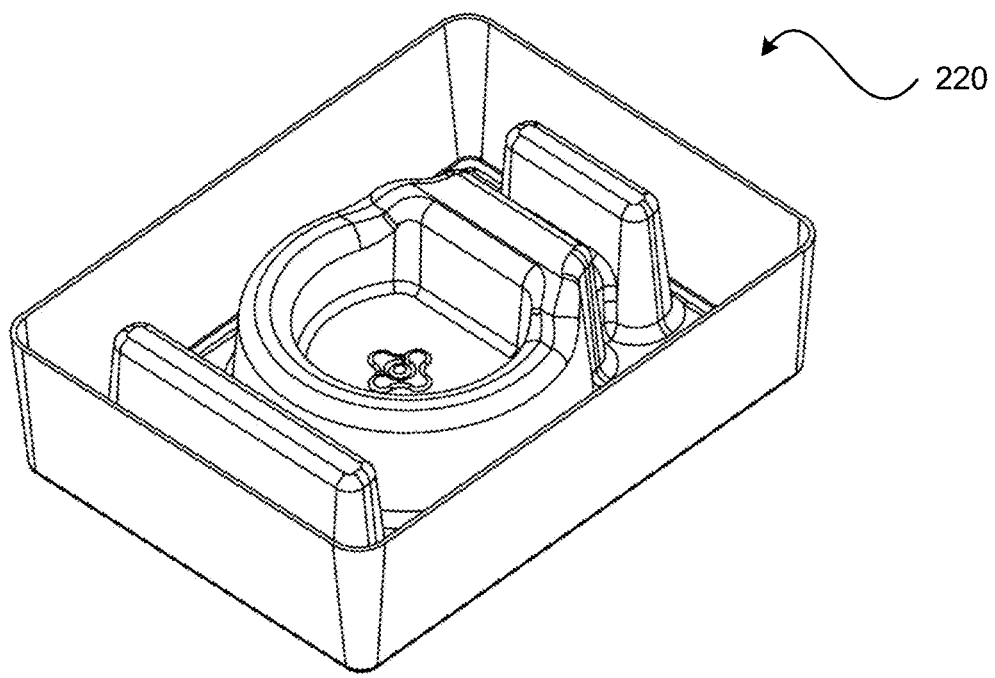
FIG. 6C is an isometric view from below, of the moulded tray of FIG. 6B.

An example of a tool 500 utilised to release data logger 110 from casing 120 is illustrated in FIGS. 5A and 5B. Tool 500 has a handle portion 510 which can be gripped by a user and a lever extension 520 which is inserted into a corresponding void formed between the casing 120 and bezel 150 and used as a lever to overcome the friction fit that otherwise holds the two parts together. Ideally the void is sized and shaped to be unobtrusive and difficult to utilise to separate the casing 120 and bezel 150 in the absence of tool 500.

Ideally, after use the data logger is refurbished or recycled. Refurbishment of data logger 110 may involve removing and discarding the bezel 150 and transparent protector 140, inspecting the data logger, cleansing existing data stored on the memory component, loading testing firmware via contact couplings 114, conducting functional testing, loading production firmware, charging or replacing the battery, placing the data logger in sleep mode and, if appropriate, fitting a new transparent protector and bezel. At the conclusion of the refurbishment process, data logger 110 is entirely reconditioned and satisfies the requirements of a newly manufactured data logger. Since the data logger 110 is uncontaminated by the first use and other components of the wearable device are new, there is no risk of contamination by transfer of bioburden from the wearable device.

Figure 7:
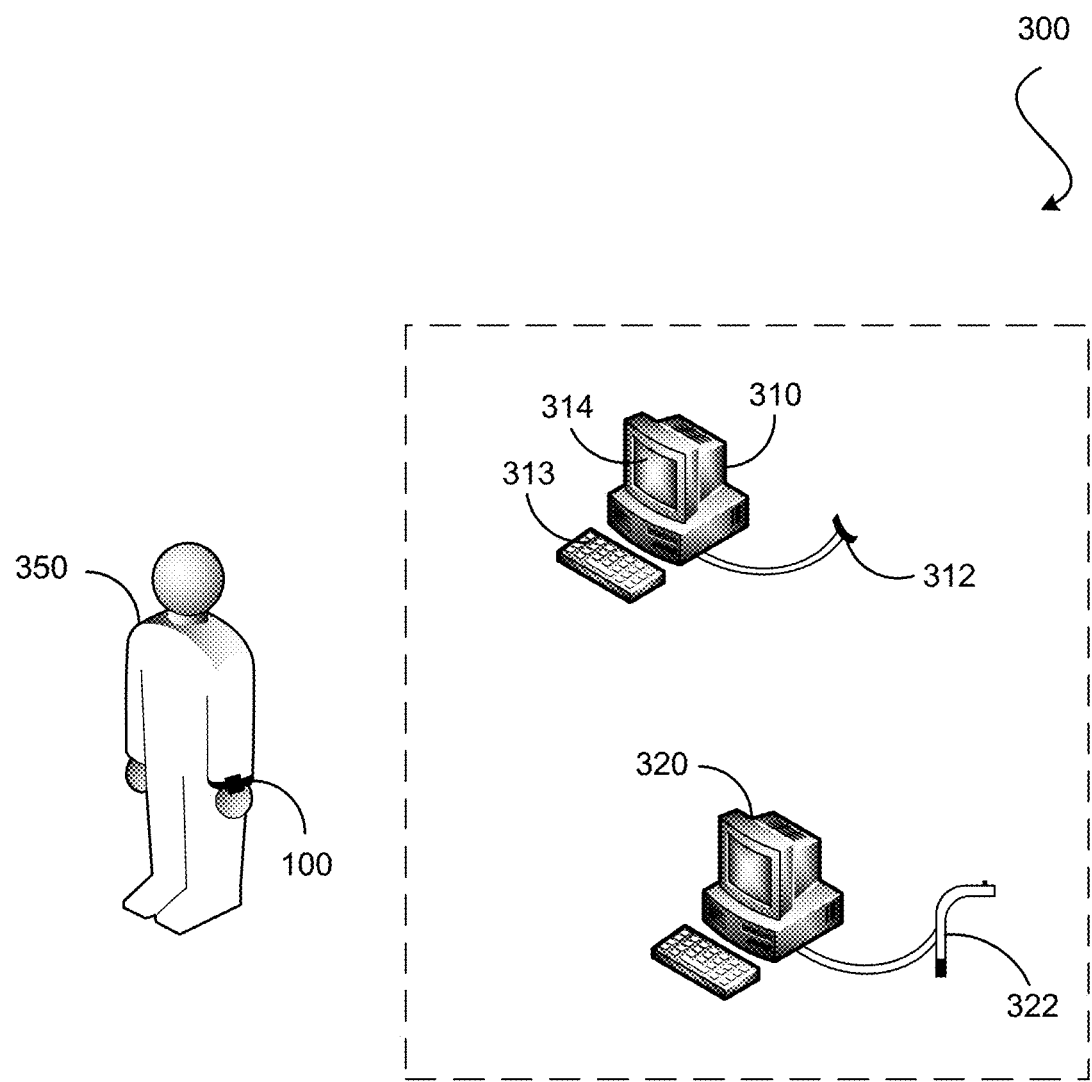
FIG. 7 is a schematic illustration of a system for recording motion data in a subject, according to an embodiment of the disclosure.

FIG. 7 is a schematic illustration of a system 300 for recording motion data in a subject 350, according to an embodiment of the disclosure. The system includes a wearable device 100 as described above, a configuration terminal 310 and an analysis terminal 320. Configuration terminal 310 has a processor (not shown) and a communicative coupling 312 adapted to connect with contact couplings 114 of the data logger 110. Configuration terminal 310 is operable to configure data logger 110 to record motion data for a specific subject 350 while wearing the device 100. Configuration terminal 310 includes a user input device such as a keyboard 313 or touch screen 314 receiving inputs from an entity, such as a person or application. The inputs enable the data logger 110 to be configured for use in recording motion data for a specific subject.

The configuration inputs may include data that is specific to the subject such as e.g. name, date of birth, medications prescribed, concurrent therapies in place such as device assisted therapies (e.g. Deep Brain Stimulation—DBS) and bodily location of the device 100 during wear (e.g. left or right wrist, chest, left or right ankle etc.). Additionally, the inputs may include data that is specific to a treating clinician of the specific subject, such as the clinician's name and location, contact details and the like. Configuration terminal 310 configures data logger 110 by transmission of a configuration file that is based on the configuration inputs, from the configuration terminal processor, to the device using a docking station or cable 312 contacting contact couplings 114 of the data logger 110 being configured although wireless transmission is also contemplated. Ideally, the data logger 110 is configured for ambulatory and continuous recording of motion data for subjects having Parkinson's disease or other diseases that involve movement disorders although the subject need not have a movement disorder to benefit from use of the device to record motion data.

Once data logger 110 is configured it is clipped into a casing 120 having a strap 130 and packed into the carton 210 with tray 220 for dispatch via a delivery service a subject 350 for assessment. Subject 350 receives carton 210, removes device 100 and wears it for the period indicated in the instructions printed on a paper insert provided in carton 210 or printed on the carton's inside lid surface 214. Typically the period of wear (and recording of motion data) is 6 to 10 days. In some examples, the battery contained within data logger 110 is sufficient for a period of continuous monitoring of 6 to 10 days, i.e. the subject does not need to charge the data logger during the period of wear. In some embodiments, the battery contained within data logger 110 is sufficient for a period of continuous monitoring of up to 28 days.

At the conclusion of the monitoring period, subject 350 replaces the device 100 in the tray 220 in carton 210, and fastens carton lid 212 closed by removing release liner 215 from adhesive strip 216 on the lip 211 and closing the container as described above. In a preferred embodiment, the data logger processor is configured to cause screen 112 to display an envelope or other icon or text indicating to the subject that the monitoring period has ended. Alternatively/ additionally a loudspeaker or vibrational element of data logger 110 may provide an audible and/or haptic cue, respectively, that the monitoring period has ended.

The subject returns the carton 210 which is fastened closed and contains the device 100 with subject-specific motion data stored on data logger 110 to a recipient. Return of carton 210 containing the device 100 is typically enabled by a prepaid shipping label which is printed onto or affixed to carton 210 prior to dispatch to subject 350.

Upon receipt of carton 210 from the subject, the data logger 110 is released from the casing 120 and strap 130, typically using a special tool, and discards the casing, strap and packaging. The stored motion data is extracted from data logger 110 by analysis terminal 320. This is achieved by connecting contact couplings 114 on the logger 110 with a docking station 322 or cable that permits transmission of the motion data from the memory component to the analysis terminal 320 for processing and/or using wireless transmission. The analysis terminal 320 may, in some embodiments, reside in docking station 322 or the docking station may, like cable 312, connect with the terminal e.g. via a USB input. Although the analysis terminal 320 is shown as separate from configuration terminal 310 and docking station 322, it is to be understood that this is for illustrative purposes and to facilitate explanation. Thus, a single terminal may be utilised to provide the configuration and analysis functions although these functions may be distributed across different terminals or indeed across different networks of interconnected processing devices.

Analysis terminal 320 is operable to extract subject-specific motion data stored on data logger 110 and generate one or more subject-specific reports from the extracted data which present objective characteristics of the movement disorder symptoms evident in motion data recorded for the specific subject. An example of pages from a report of the type contemplated is illustrated in FIGS. 8A to 8F. Objective characteristics that may be presented or analysed in reports generated by analysis terminal 320 include but are not limited to graphs 810, 811 charting dyskinetic and bradykinetic behaviour over time respectively, a table 812 presenting patient results calculated by a processor of analysis terminal 320 and reporting on objective measures such as e.g. Median Dyskinesia Score (DKS), percentage of time spent in Dyskinesia (PTD), Median Bradykinesia Score (BKS), percentage of time spent in tremor (PTT), percentage of time spent immobile (PTI), number of steps taken, Dosage Compliance, Fluctuations in Dyskinesia score (FDS), DBS selection score and the like.

Report 800 may include a notes region 820 for including non-chart and non-tabular information such as a legend indicating the meaning of symbols appearing in charts 810, 811 e.g. where a capsule icon 821 indicates presentation of a medication reminder to the subject during assessment and a vertical line 822 denotes a medication acknowledgement input by the subject. Notes region 820 may also include text or graphical notes manually added by a technician curating the report generated automatically by the processor of analysis terminal 320, prior to the report being dispatched to a clinician for use in determining progress or treatment of the subjects' movement disorder symptoms.

Figure 8A:
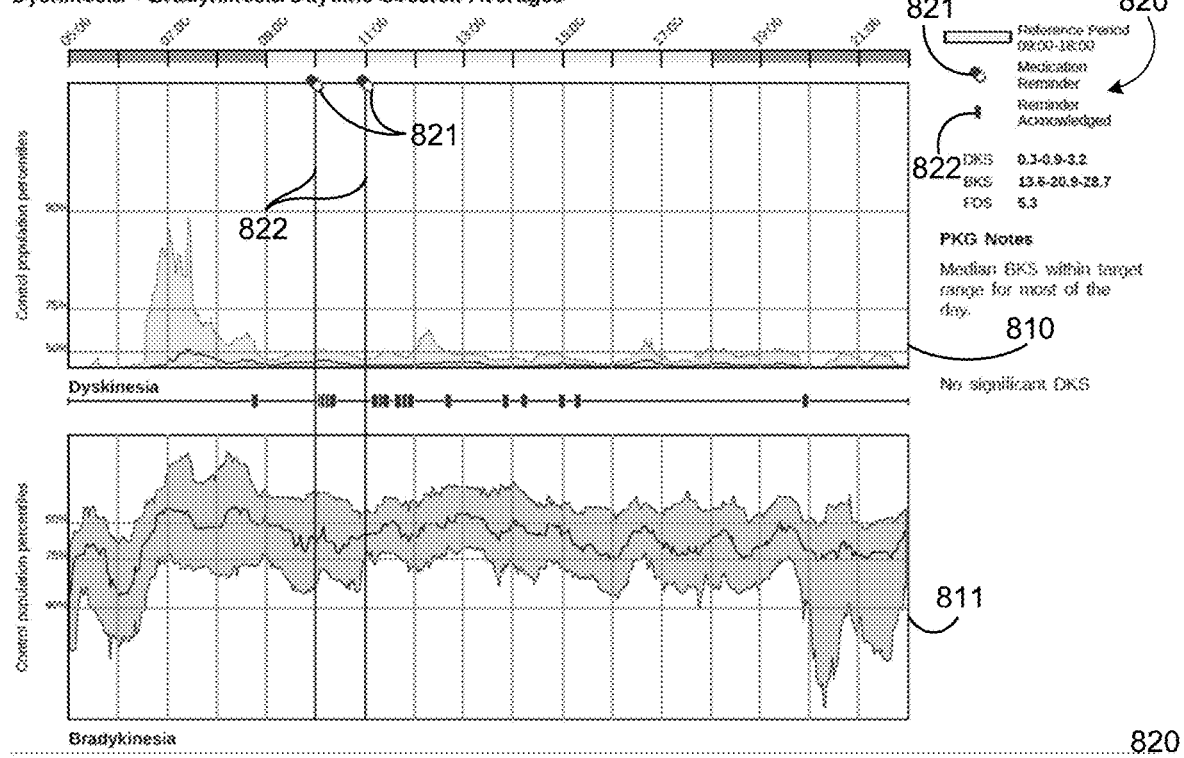
Figure 8B:
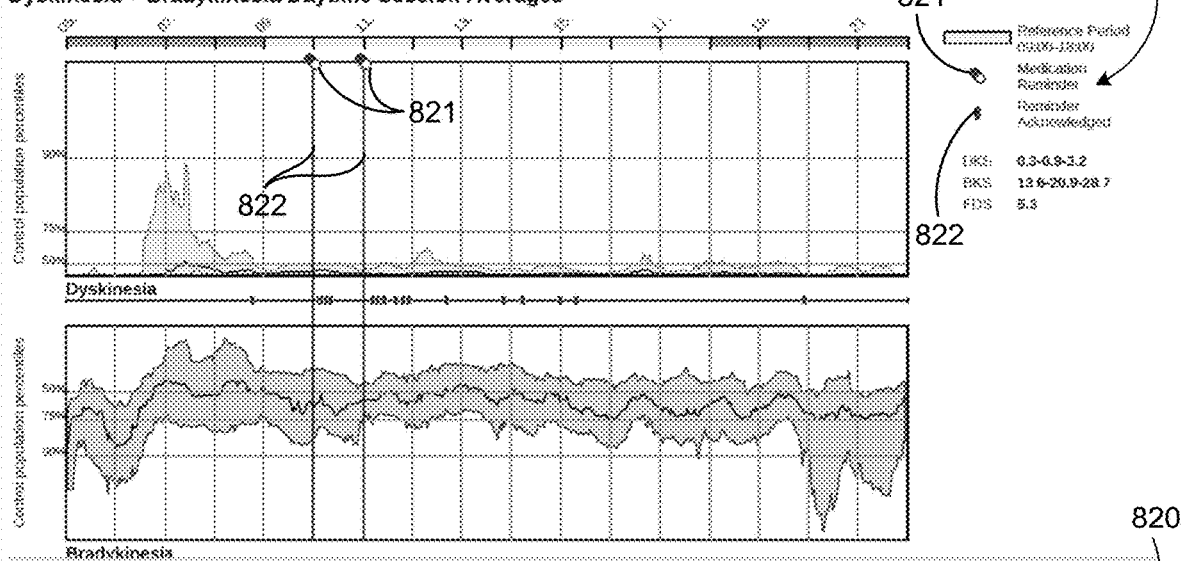
Figure 8B:
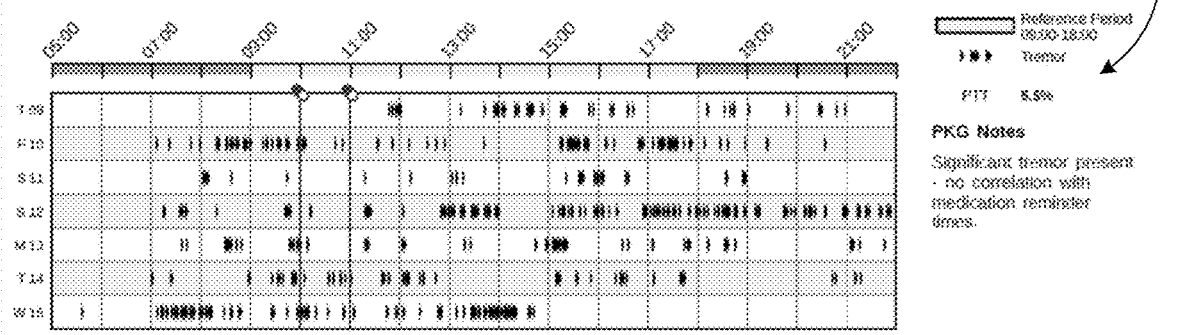
Figure 8B:
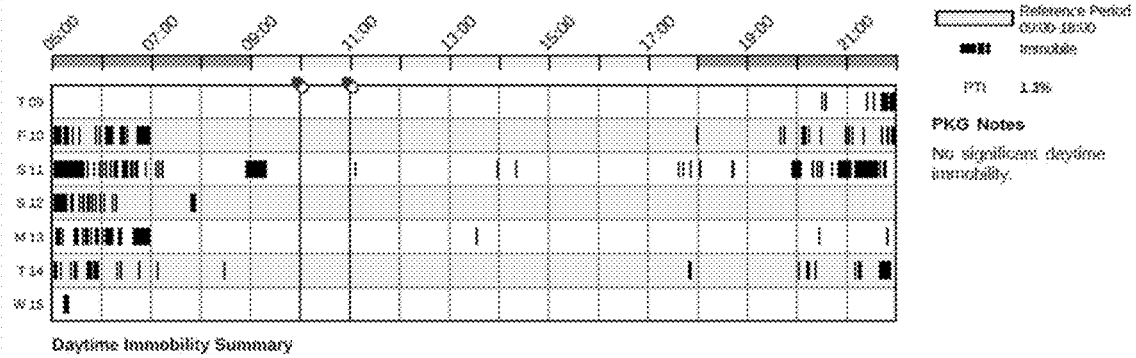
Figure 8C:
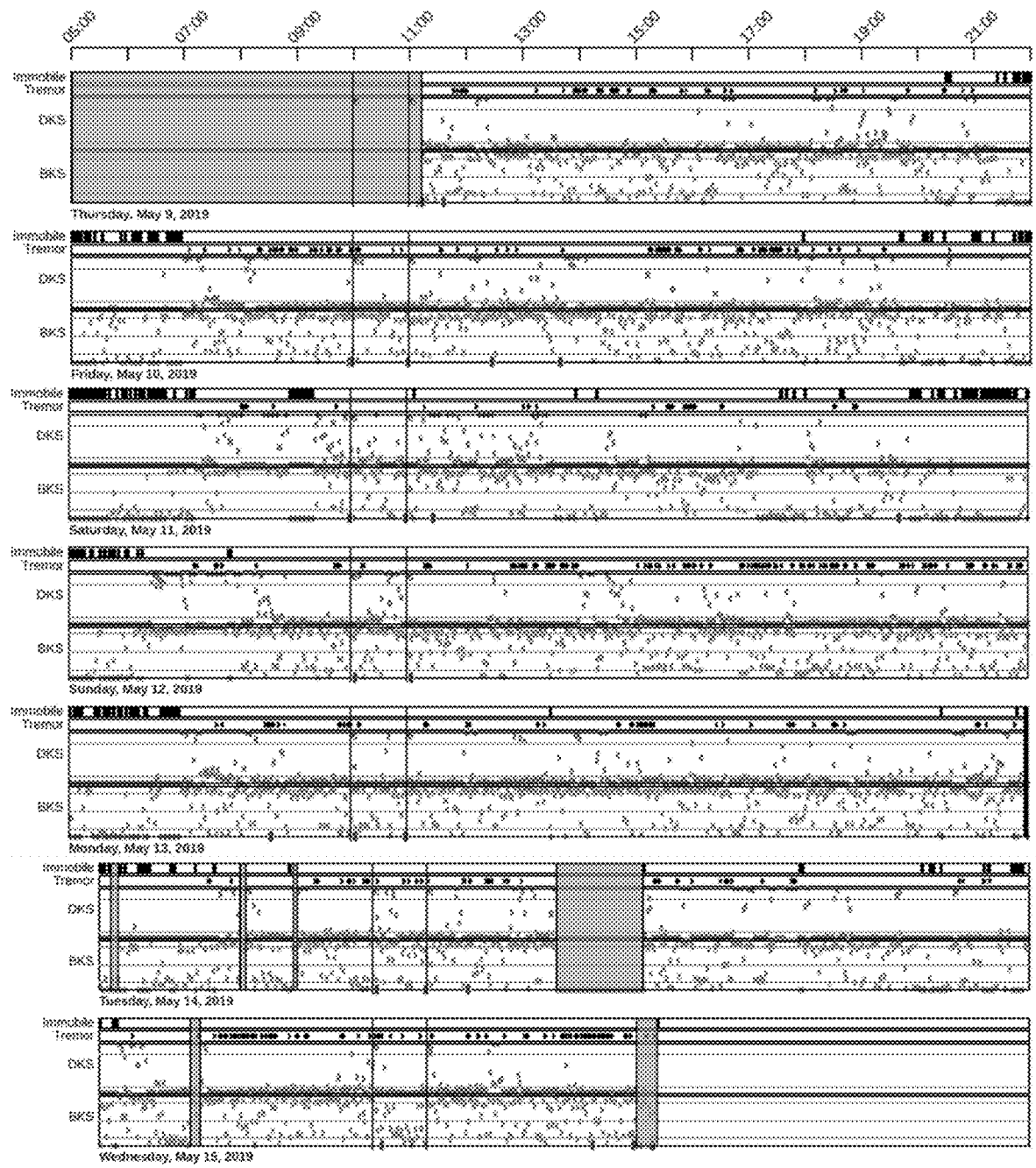
Figure 8D:
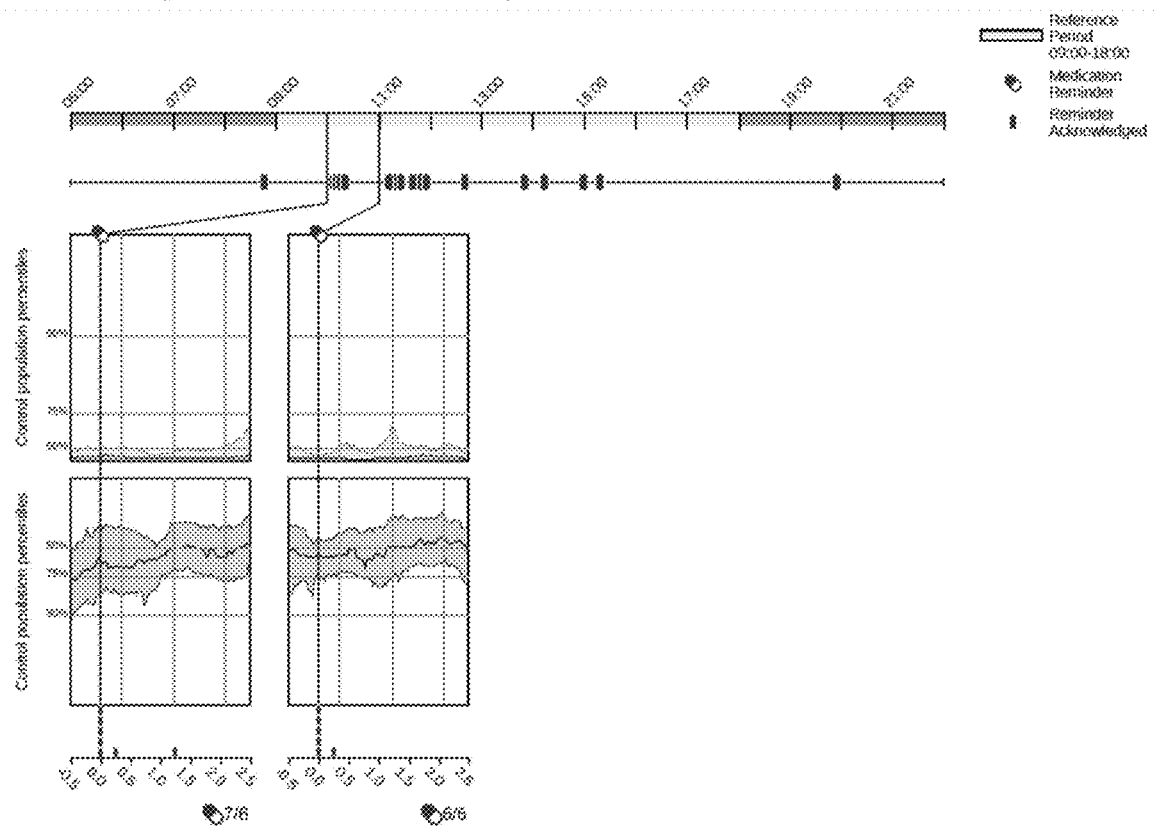

Report 800 may take any suitable form however in some embodiments the report is divided into sections that include e.g. Daytime Session average scores for BK and DK, Daytime Patient Results, Daytime Summaries (e.g. for tremor and immobility although other measures could be indicated), Nighttime Summaries, and Daily plots for various measures that can be obtained by from the motion data. The report may also indicate time periods when device 100 is off the subject's wrist. The processor may generate the report including, as shown in FIG. 8D, expanded time periods following key events such as medication reminders or medication acknowledgements, to provide more detailed views of motion data collected during periods of time following those events. The report may also include, as shown in FIG. 8E, longitudinal views of measures such as DK and BK. The longitudinal views may be generated automatically by the analysis terminal processor which accesses a repository of motion data previously obtained from the subject for whom the report is being generated. The report may also include a Summary section as exemplified in FIG. 8F.

In some embodiments, system 300 includes a specially designed a tool 500 for releasing the data logger from the casing.

Advantageously, the present disclosure provides a wearable device for recording motion data, and a kit and system therefor, for assessment of subjects having movement disorder diseases such as Parkinson's disease. Thus, subjects having symptoms of a movement disorder can, after initial consultation from their clinician, receive a kit, or carton containing the device and everything that is needed to complete functional assessment without the requirement to attend a clinic, or undertake task based tests as has been the case in the past. Rather, the subject opens the carton, applies the wearable device like a wrist watch, and carries on with daily living with minimal interference, inconvenience and negative impact. In one example, aside from a wrist-worn wearable device, no sensors are required to be placed elsewhere on the body and no specific configuration of the device is required to be performed by the subject who is ambulatory and burden free.

Owing to the arrangement of the data logger component of the wearable inside a protective casing and elements that prevent the subject from physically contacting the data logger, the device is robust in that there can be no interference by the subject in the configuration of the device e.g. due to cognitive or physical impairment. Additionally, concealment of contact couplings within the casing can minimise the risk of unauthorised or unintended dissemination of motion and other data stored on the memory component of the data logger. These aspects, combined with features of the device relating to medication reminders and acknowledgements give rise to high patient compliance, both with medication regimens and wearing of the device for the assessment duration enabling collection of continuous, high quality motion data.

A clinician may have on hand one or more data loggers, or may order them from a supplier, and may utilise a configuration terminal to configure the data logger for a specific subject who is a patient of the clinician. In such an arrangement, the clinician would connect a cable or docking station adapted to connect with contact couplings, typically on the back of the data logger, to his or her computer. The computer may be configured with software to generate a configuration file and push that to the data logger processor, or to log on to a web based or remotely hosted application that enables the configuration file to be created and pushed, via the cable or docking station, to the data logger. Once configured, the clinician secures the data logger in a casing with a strap, places it into the tray and dispatches the kit to the subject. After the subject has utilised the device it is returned to a recipient for data extraction and reports generated by the analysis terminal are delivered electronically to the clinician.

In other embodiments, a clinician may utilise an ordering system, ideally an online ordering system which enables the clinician to enter various subject and clinician—specific input parameters that enable a third party to configure a device and deliver it directly to the subject. After the subject has utilised the device, it is returned for data extraction and analysis and reports generated by the analysis terminal are delivered electronically to the treating clinician. This eliminates the need for the clinician to hold and handle stock and technology with which it may not be familiar, yet ensures that the clinician can swiftly order the service and receive reports delivered as part of the service.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components or group thereof.

It is to be understood that various modifications, additions and/or alterations may be made to the parts previously described without departing from the ambit of the present disclosure as defined in the claims appended hereto.

Future patent applications may be filed in the United States of America or overseas on the basis of or claiming priority from the present application. It is to be understood that the following claims are provided by way of example only, and are not intended to limit the scope of what may be claimed in any such future application. Features may be added to or omitted from the claims at a later date so as to further define or re-define the invention or inventions.

The claims are as follows:

1. A wearable device for recording motion data, the wearable device comprising:
   a. a data logger having a battery, a motion sensor configured to detect movement of the wearable device when worn by a subject, and a memory component configured to store motion data from the motion sensor;
   b. a casing and a bezel together configured for retaining the data logger;
   c. one or more fasteners configured to couple the bezel with the casing to securely retain the data logger in the casing; and
   d. a strap attached to or integral with the casing for wearing by the subject;
       wherein the data logger has side walls, an under-surface, and a screen on an upper surface thereof, and
       wherein the casing and the bezel together form a contact barrier that prevents contact contamination between the subject and the side walls and under-surface of the data logger while the wearable device is worn by the subject for collection and storage of subject-specific motion data, and
       wherein the one or more fasteners are operable only by use of a tool to control release of the data logger from the casing in a substantially uncontaminated state.

2. The wearable device according to claim 1, wherein the data logger includes contact couplings for coupling with a docking station or cable, and wherein the contact couplings are inaccessible when the data logger is securely retained in the casing.

3. The wearable device according to claim 1, wherein the wearable device includes a transparent protector providing a contact barrier between the screen and the subject.

4. The wearable device according to claim 3, wherein the bezel, the casing, and the transparent protector substantially prevent contact contamination of the data logger including the screen by the subject.

5. The wearable device according to claim 1, wherein the data logger includes a processor that is configurable to present the subject with one or medication reminders based on subject-specific parameters received during configuration of the wearable device.

6. The wearable device according to claim 5, wherein the data logger includes one or more of:
   a. a loudspeaker and the one or more medication reminders are presented as an audible prompt emitted from the loudspeaker;
   b. a screen and the one or more medication reminders are presented as a visible prompt presented on the screen; and
   c. a vibrating element and the one or more medication reminders are presented as a haptic prompt presented by the vibrating element.

7. The wearable device according to claim 2, wherein the data logger is configurable to communicate with an external processor via the contact couplings, and the external processor is adapted to perform one or more of:
   a. configuring the data logger for wear by the subject during an assessment period;
   b. processing motion data stored by the data logger;
   c. generating a report based on processed motion data from the data logger; and
   d. reconditioning the data logger after wear by the subject.

8. The wearable device according to claim 1, wherein the data logger is adapted to be refurbished or recycled.

9. The wearable device according to claim 8, wherein the casing and the strap are disposable or recyclable.

10. The wearable device according to claim 1, wherein the data logger is operable for continuous recording of motion data that is indicative of presence or absence of movement disorder symptoms and behaviours selected from a group including: bradykinesia, dyskinesia, tremor, fluctuations, immobility and gait.

11. The wearable device according to claim 1, wherein the data logger is operable for continuous recording of motion data for a minimum of 72 hours up to 10 days.

12. The wearable device according to claim 1, wherein the data logger includes a sensor for determining if the wearable device is being worn by the subject.

13. A kit for recording motion data, the kit comprising:
   a wearable device comprising a data logger having a battery, a motion senso r configured to detect movement of the wearable device when worn by a subject, a memory component configured to store motion data from the motion sensor, a casing and a bezel together configured for retaining the data logger, and one or more fasteners configured to couple the bezel with the casing to securely retain the data logger in the casing, and a strap attached to or integral with the casing for wearing by the subject, wherein the data logger has side walls, an under-surface, and a screen on an upper surface thereof, and wherein the casing and the bezel together form a contact barrier that prevents contact contamination between the subject and the side walls and under-surface of the data logger while the wearable device is worn by the subject for collection and storage of subject-specific motion data, and wherein the one or more fasteners are operable only by use of a tool to control release of the data logger from the casing in a substantially uncontaminated state;
   a. a tray for receiving the wearable device; and
   b. a carton for housing the tray and the wearable device during delivery of the wearable device to and from the subject, the carton having a fastening portion operable by the subject to fasten the carton closed for delivery of the device, storing motion data from the subject, to a recipient.

14. The kit according to claim 13, wherein the tray is moulded to receive one or more accessories for the wearable device, the accessories including but not limited to:
   a. a cleaning cloth; and
   b. a strap extension.

15. The kit according to claim 13, wherein the tray is moulded to receive the casing and strap separately from the data logger.

16. The kit according to claim 13, wherein the carton has a foldable closure and the fastening portion includes an adhesive with a removable release liner on the foldable closure.

17. The kit according to claim 13, wherein the carton is pre-marked with a recipient location and postal authority for delivery of the carton and contents from the subject to the recipient location.

18. The kit according to claim 13, wherein the carton includes a foldable lid having an inside panel displaying one or both of instructions for use of the device and instructions for sending the used device storing motion data from the subject, in the carton, to the recipient.

19. The kit according to claim 13, wherein the wearable device includes a transparent protector providing a contact barrier between the screen and the subject.

20. The kit according to claim 13, wherein the data logger is adapted to be refurbished or recycled.

21. A system for recording motion data for a subject, the system comprising:
   a wearable device comprising: a data logger having a battery, a motion sensor configured to detect movement of the wearable device when worn by the subject, a memory component storing motion data from the motion sensor, a casing and a bezel together configured for retaining the data logger, one or more fasteners configured to couple the bezel with the casing to securely retain the data logger in the casing, and a strap attached to or integral with the casing for wearing by the subject, wherein the data logger has side walls, an under-surface, and a screen on an upper surface thereof, and wherein the casing and the bezel together form a contact barrier that prevents contact contamination between the subject and the side walls and under-surface of the data logger while the wearable device is worn by the subject for collection and storage of subject-specific motion data, and wherein the one or more fasteners are operable only by use of a tool to control release of the data logger from the casing in a substantially uncontaminated state;
   a. a configuration terminal comprising a processor and a communicative coupling adapted to communicate with the data logger, the configuration terminal being operable to configure the data logger to record motion data for a specific subject; and
   b. an analysis terminal comprising a processor and a communicative coupling adapted to communicate with the data logger, the analysis terminal being operable to extract subject-specific motion data stored on the data logger and generate one or more subject-specific reports from the subject-specific motion data which present objective characteristics of the subject-specific motion data recorded for the specific subject.

22. The system according to claim 21, wherein the configuration terminal configures the data logger by transmission, through the communicative coupling, of a configuration file containing configuration data pertaining to one or more of:
   a. prescribing or treating clinician;
   b. the subject;
   c. body location of the wearable device during wear;
   d. medication prescribed to the subject; and
   e. concurrent therapies including device assisted therapies.

23. The system according to claim 21, wherein objective characteristics presented in the one or more subject-specific reports generated by the analysis terminal include:
   a. graphs charting bradykinetic and/or dyskinetic behaviour over time;
   b. values representing amount or proportion of time spent in one or more of bradykinesia, dyskinesia, tremor, immobile, inactive, active;
   c. values representing a bradykinesia or dyskinesia score, quality of sleep, and sleep fragmentation;
   d. number of steps taken;
   e. medication dosage compliance;
   f. fluctuations;
   g. device assisted therapy suitability;
   h. quality of sleep;
   i. medication reminders provided;
   j. medication acknowledgements; and
   k. target ranges for one or more objective parameters contained in the one or more subject-specific reports, such as bradykinesia and dyskinesia.

24. The system according to claim 21, wherein the data logger has one or more contact couplings for coupling with one or both of the configuration terminal and the analysis terminal using a cable or docking station; and wherein the one or more contact couplings are inaccessible when the data logger is retained in the casing and bezel.

25. The system according to claim 21, further including the tool for releasing the data logger from the casing.

* * * * *